US012426961B2

(12) United States Patent
Mirar

(10) Patent No.: US 12,426,961 B2
(45) Date of Patent: Sep. 30, 2025

(54) SYSTEM AND METHOD FOR AUTOMATIC MEDICAL DEVICE PLACEMENT IN AN ANATOMICAL STRUCTURE USING A LOCKING MECHANISM

(71) Applicant: GE Precision Healthcare LLC, Waukesha, WI (US)

(72) Inventor: Hani Nozari Mirar, Oslo (NO)

(73) Assignee: GE Precision Healthcare LLC, Waukesha, WI (US)

(*) Notice: Subject to any disclaimer, the term of this patent is extended or adjusted under 35 U.S.C. 154(b) by 208 days.

(21) Appl. No.: 18/368,370

(22) Filed: Sep. 14, 2023

(65) Prior Publication Data

US 2025/0090247 A1   Mar. 20, 2025

(51) Int. Cl.
*A61B 34/10* (2016.01)
*A61B 17/12* (2006.01)
*A61B 34/00* (2016.01)
*A61B 34/20* (2016.01)
*A61B 90/00* (2016.01)
*A61M 25/01* (2006.01)

(52) U.S. Cl.
CPC ........ *A61B 34/25* (2016.02); *A61B 17/12122* (2013.01); *A61B 2034/107* (2016.02); *A61B 2034/2063* (2016.02); *A61B 2034/2065* (2016.02); *A61B 2090/378* (2016.02); *A61M 2025/0166* (2013.01)

(58) Field of Classification Search
CPC .................. A61B 2034/2063; A61B 2034/107
See application file for complete search history.

(56) References Cited

U.S. PATENT DOCUMENTS

| 6,755,854 B2* | 6/2004 | Gillick ...................... A61F 2/95 |
| | | 623/1.11 |
| 10,588,597 B2* | 3/2020 | Zhao ...................... A61B 34/10 |

(Continued)

OTHER PUBLICATIONS

Leventic, Hrvoje, et al. "A Survey of Left Atrial Appendage Segmentation and Analysis in 3D and 4D Medical Images." The 28th International Conference on Systems, Signals and Image Processing, IWSSIP 2021, Proceedings, 2021.

(Continued)

*Primary Examiner* — Colin T. Sakamoto
(74) *Attorney, Agent, or Firm* — McAndrews, Held & Malloy, Ltd.; Daniel Bissing; David Bates

(57) ABSTRACT

Systems and methods for placement of a medical device in an anatomical structure using a locking mechanism are provided. The method includes performing one or more ultrasound image acquisitions, detecting and tracking one or more anatomical structures in the one or more ultrasound image acquisitions, causing a display system to present a volume of a region of interest within or surrounding the one or more anatomical structures in the one or more ultrasound image acquisitions, processing the one or more ultrasound image acquisitions to identify a first location corresponding to a target placement location within the region of interest for a medical device, processing the one or more ultrasound image acquisitions to identify a second location corresponding to a location of a catheter including the medical device, and outputting a signal to deploy the medical device when the second location matches the first location.

20 Claims, 8 Drawing Sheets

(56) References Cited

U.S. PATENT DOCUMENTS

| | | | | |
|---|---|---|---|---|
| 11,957,424 | B2* | 4/2024 | Donhowe | A61B 34/74 |
| 12,303,203 | B1* | 5/2025 | Boveja | G06F 3/011 |
| 2004/0034297 | A1* | 2/2004 | Darrow | A61B 34/20 |
| | | | | 600/407 |
| 2014/0073911 | A1* | 3/2014 | Munrow | A61B 5/066 |
| | | | | 600/424 |
| 2016/0354057 | A1* | 12/2016 | Hansen | A61B 8/483 |
| 2017/0135760 | A1* | 5/2017 | Girotto | A61B 34/20 |
| 2018/0368807 | A1* | 12/2018 | Van De Pas | A61B 34/20 |
| 2019/0183577 | A1* | 6/2019 | Fahim | G02B 27/01 |
| 2024/0206906 | A1* | 6/2024 | Highsmith | A61B 17/3478 |
| 2025/0017554 | A1* | 1/2025 | Miyaki | A61B 8/463 |

OTHER PUBLICATIONS

Jin, Cheng, et al. "Left atrial appendage segmentation and quantitative assisted diagnosis of atrial fibrillation based on fusion of temporal-spatial information." Computers in Biology and Medicine, vol. 96, 2018, pp. 52-68.

Wang, Lei et al. "Left atrial appendage segmentation based on ranking 2-D segmentation proposals." Statistical Atlases and Computational Models of the Heart. Imaging and Modelling Challenges: 7th International Workshop, STACOM 2016, Held in Conjunction with MICCAI 2016, Athens, Greece, Oct. 17, 2016, Revised Selected Papers 7. Springer International Publishing, 2017.

* cited by examiner

SYSTEM AND METHOD FOR AUTOMATIC MEDICAL DEVICE PLACEMENT IN AN ANATOMICAL STRUCTURE USING A LOCKING MECHANISM

FIELD

Certain embodiments relate to ultrasound imaging. More specifically, certain embodiments relate to a method and system for placing a medical device in an anatomical structure using a locking mechanism.

BACKGROUND

Ultrasound imaging is a medical imaging technique for imaging anatomical structures, such as organs and soft tissues, in a human body. Ultrasound imaging uses real time, non-invasive high frequency sound waves to produce two-dimensional (2D), three-dimensional (3D), and/or four-dimensional (4D) (i.e., real-time/continuous 3D images) images.

Ultrasound imaging is a powerful tool for real-time heart (e.g., muscle and chambers) movement visualization and is used for the placement of medical devices in and around organs and soft tissues. However, current methods and ultrasound systems for the placement of medical devices do not sufficiently guide a physician when placing a medical device on organs and tissues that are actively moving and do not automatically and accurately place medical devices in or around organs and tissues.

For example, medical devices may be placed in the left atrial appendage of a heart. However, the left atrial appendage is dynamic, and it may be difficult to provide accurate timing to place the probe in the correct position to provide proper placement of the medical device in the left atrial appendage.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for automatically placing a medical device in an anatomical structure using a locking mechanism, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
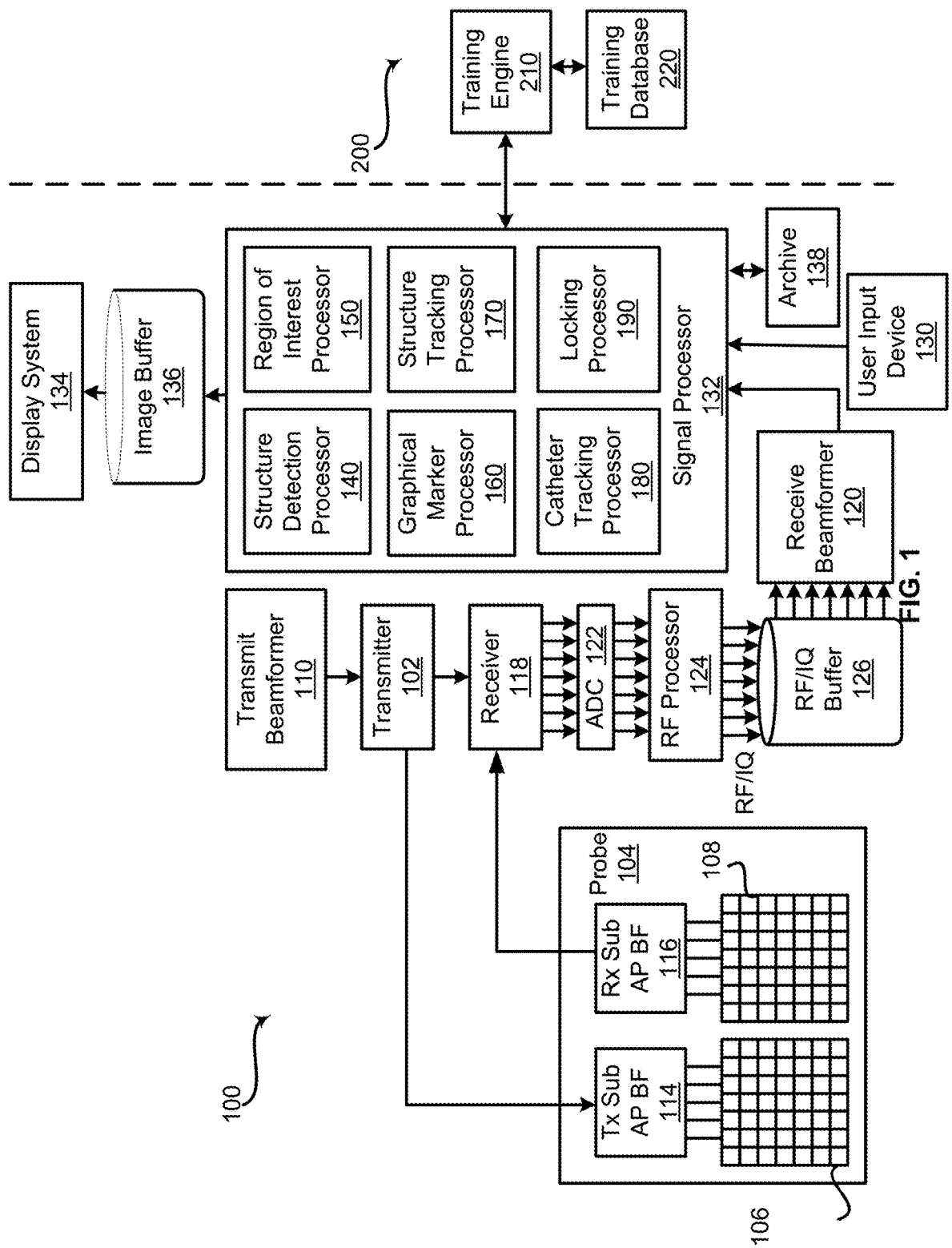
FIG. 1 is a block diagram of an exemplary ultrasound system that is operable for automatically placing a medical device in an anatomical structure using a locking mechanism, in accordance with various embodiments.

Certain embodiments may be found in a method and system for automatically placing a medical device in an anatomical structure using a locking mechanism. Aspects of the present disclosure have the technical effect of automatically providing real-time feedback regarding the placement of a medical device in a target placement location of an anatomical structure and the location of the medical device with respect to target placement location in a live ultrasound scan. Various embodiments have the technical effect of processing acquired ultrasound images to identify a target placement location for a medical device and a current location of a medical device in a live ultrasound scan. Certain embodiments have the technical effect of overlaying the live ultrasound scan with a first graphical maker and a second graphical marker representing the target placement location and the current location of the medical device in a live ultrasound scan. Aspects of the present disclosure have the technical effect of updating the rendering, the first marker, and the second marker dynamically over time. Various embodiments have the technical effect of automatically deploying the medical device in the target placement location using a locking mechanism.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical, and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment." "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode, which can be one-dimensional (1D), two-dimensional (2D), three-dimensional (3D), or four-dimensional (4D), and comprising Brightness mode (B-mode), Motion mode (M-mode), Color Motion mode (CM-mode), Color Flow mode (CF-mode), Pulsed Wave (PW) Doppler, Continuous Wave (CW) Doppler, Contrast Enhanced Ultrasound (CEUS), and/or sub-modes of B-mode and/or CF-mode such as Harmonic Imaging. Shear Wave Elasticity Imaging (SWEI), Strain Elastography, Tissue Velocity Imaging (TVI), Power Doppler Imaging (PDI), B-flow, Micro Vascular Imaging (MVI), Ultrasound-Guided Attenuation Parameter (UGAP), and the like.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), Digital Signal Processor (DSP), Field-Programmable Gate Array (FPGA), Application-Specific Integrated Circuit (ASIC), or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system that is operable to automatically place a medical device in an anatomical structure using a locking mechanism, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, analog-to-digital (A/D) converters 122, a radio frequency (RF) processor 124, a RF quadrature (RF/IQ) buffer 126, a user input device 130, a signal processor 132, an image buffer 136, a display system 134, and an archive 138.

The transmitter 102 may comprise suitable logic, circuitry, interfaces, and/or code that may be operable to drive an ultrasound probe 104. The ultrasound probe 104 may comprise a two dimensional (2D) array of piezoelectric elements. In certain embodiments, the ultrasound probe 104 is a transesophageal ultrasound probe. The ultrasound probe 104 may comprise a group of transmit transducer elements 106 and a group of receive transducer elements 108, that normally constitute the same elements. The group of transmit transducer elements 106 may emit ultrasonic signals through oil and a probe cap and into a target. In a representative embodiment, the ultrasound probe 104 may be operable to acquire ultrasound image data covering at least a substantial portion of an anatomy, such as a heart, an ovary, or any suitable anatomical structure. In an exemplary embodiment, the ultrasound probe 104 may be operated in a volume acquisition mode, where the transducer assembly of the ultrasound probe 104 acquires a plurality of parallel 2D ultrasound slices forming an ultrasound volume.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, and interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces, and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces, and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select target structures for automatic detection and tracking, input and/or select a region of interest, modify a region of interest, select regions of interest and/or activatable buttons corresponding with regions of interest used to acquire a focused/zoomed volume, and the like. Alternatively or additionally, the user input device 130 may be utilized to place graphical markers on structures, regions of interest, medical devices, etc. In an exemplary embodiment, the user input device 130 may be operable to configure, manage, and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera, and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a structure detection processor 140, a region of interest processor 150, a graphical marker processor 160, a structure tracking processor 170, a catheter tracking processor 180, and a locking processor 190. The signal processor 132 may be capable of receiving input information from a user input device 130 and/or archive 138, generating an output displayable by a display system 134, and manipulating the output in response to input information from a user input device 130, among other things. The signal processor 132, structure detection processor 140, region of interest processor 150, graphical marker processor 160, structure tracking processor 170, catheter tracking processor 180, and locking processor 190 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a structure detection processor 140 that comprises suitable logic, circuitry, interfaces, and/or code that may be operable to analyze acquired ultrasound images and/or volumes to detect a presence and location of anatomical structures in the ultrasound images and/or volumes. In this regard, the structure detection processor 140 may include, for example, image analysis algorithms, one or more deep neural networks (e.g., a convolutional neural network such as u-net) and/or may utilize any suitable form of image analysis techniques, artificial intelligence, or machine learning processing functionality configured to detect and localize anatomical structures in ultrasound images and/or volumes. Additionally and/or alternatively, the image analysis techniques, artificial intelligence, or machine learning processing functionality configured to detect and localize anatomical structures in ultrasound images and/or volumes may be provided by a different processor or distributed across multiple processors at the ultrasound system 100 and/or a remote processor communicatively coupled to the ultrasound system 100. For example, the structure detection and localization functionality may be provided as a deep neural network that may be made up of, for example, an input layer, an output layer, and one or more hidden layers in between the input and output layers. Each of the layers may be made up of a plurality of processing nodes that may be referred to as neurons. For example, the structure detection and localization functionality may include an input layer having a neuron for each pixel of an ultrasound image and/or voxel of an ultrasound volume. The output layer may have a neuron corresponding to each heart muscle, heart chamber, and/or any suitable anatomical structure. Each neuron of each layer may perform a processing function and pass the processed ultrasound image information to one of a plurality of neurons of a downstream layer for further processing. As an example, neurons of a first layer may learn to recognize edges of structure in the obtained ultrasound image and/or volume. The neurons of a second layer may learn to recognize shapes based on the detected edges from the first layer. The neurons of a third layer may learn positions of the recognized shapes relative to landmarks in the obtained ultrasound image and/or volume. The processing performed by the deep neural network may identify anatomical structures and the location of the anatomical structures in the obtained ultrasound images and/or volume with a high degree of probability.

In an exemplary embodiment, the structure detection processor 140 may be configured to analyze the ultrasound images and/or volume to detect and localize a target structure. For example, the structure detection processor 140 may be configured to receive a user input selecting a target structure prior to performing an initial ultrasound image acquisition and analyzing the ultrasound image and/or volume of the initial ultrasound image acquisition to detect and localize the target structure.

Figure 2:
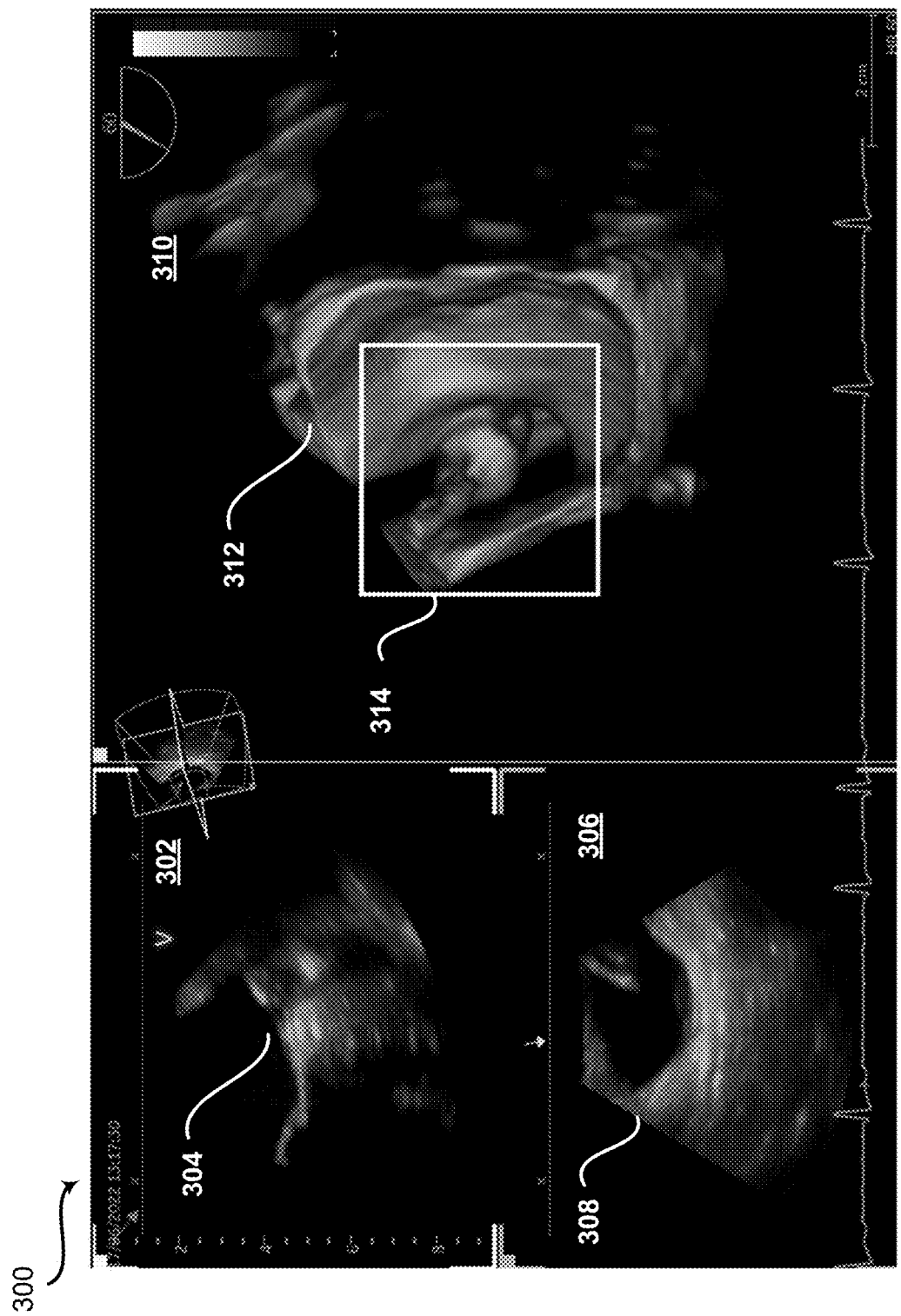
FIG. 2 is an exemplary display 300 of two-dimensional (2D) ultrasound images and a 3D/4D ultrasound image of an anatomical structure before placement of a medical device, in accordance with various embodiments.

FIG. 2 is an exemplary display 300 of two-dimensional (2D) ultrasound images 304, 308, and a 3D/4D ultrasound image 312 of an anatomical structure before placement of a medical device, in accordance with various embodiments. Referring to FIG. 2, the display 300 includes a first image display portion 302 comprising a first ultrasound image 304, a second image display portion 306 including a second ultrasound image 308, and a third display portion 310 for displaying a third ultrasound image 310. The display 300 may be provided on a main display of the display system 134 with the image display portions 302, 306, 310 as shown in FIG. 2 and/or may be provided on a touch panel of the display system 134. The third display portion may include a region of interest 314 that may be determined automatically or that may be selected by a user via user input.

A user input via a user input device 130 may trigger an initial ultrasound image acquisition by the ultrasound probe 104. The initial ultrasound image acquisition may be a 2D image acquisition, such as acquiring 2D ultrasound images for analysis by the structure detection processor 140. Additionally and/or alternatively, the initial ultrasound image acquisition may be a volume acquisition. The structure detection processor 140 may be configured to analyze the acquired volume to detect and localize the structure 312. The detected and localized target structure 312 may be provided by the structure detection processor 140 to the region of interest processor 150. Additionally and/or alternatively, the detected and localized target structure 312 may be stored at archive 138 and/or any suitable computer readable medium. Additional ultrasound image acquisitions may be acquired automatically and/or in response to a user input. The additional ultrasound image acquisitions may be 2D images, 3D/4D images, or volume acquisitions. For example, the structure detection processor 140 may automatically initiate additional ultrasound image acquisitions by the ultrasound probe 104 if a user input is not received in a predetermined period of time. As another example, the structure detection processor 140 may be configured to initiate the additional ultrasound image acquisitions by the ultrasound probe 104 in response to a user input.

The first acquired image obtained through the first image may be placed in the first image display portion 302 as a 2D ultrasound image 304, the second acquired image may be placed in the second image display portion 306 as a 2D ultrasound image 308, and a third acquired image may be placed in image display portion 310 as a 3D/4D volume 312. Although the 2D images 304, 308 and the 3D/4D image 312 are depicted in various positions on the display, the positions of the 2D ultrasound images 304, 308 and the 3D/4D image 312 may be customized and displayed in different positions on the display 400.

Referring again to FIG. 1, the structure detection processor 140 may be configured to analyze the ultrasound images and/or volume to detect and localize all anatomical structures present in the ultrasound images and/or volume. For example, the structure detection processor 140 may be configured to analyze an ultrasound image and/or volume of an initial ultrasound image acquisition to detect and localize all anatomical structures present in the ultrasound images and/or volume without and/or prior to receiving a target structure. The detected and localized anatomical structures may be provided by the structure detection processor 140 to the region of interest processor 150. Additionally and/or alternatively, the detected and localized anatomical structures may be stored at archive 138 and/or any suitable computer readable medium, and the region of interest processor 150 may obtain the detected and localized anatomical structures from the archive 138 and/or any suitable computer readable medium.

The signal processor 132 may include a region of interest processor 150 that comprises suitable logic, circuitry, interfaces and/or code that may be operable to cause a display system 134 to present an initial ultrasound image acquisition with a region of interest within, adjacent to, or surrounding a structure detected and localized by the structure detection processor 140. For example, the region of interest processor 150 may be configured to receive from the structure detection processor 140, or retrieve from the archive 138 and/or any suitable data storage medium, the identity and location of a target structure. The region of interest processor 150 may be configured to identify the localized target structure by overlaying a bounding box, colorizing pixels, a marker, and/or any suitable identification technique. The initial ultrasound image acquisition having the identified region(s) of interest may include a 2D image, 2D biplane images, 2D image slices extracted from a volume, a rendered volume, and/or any suitable ultrasound image and/or volume rendering (i.e., 2D projection of 3D/4D volume image data). The region of interest 314 may be determined automatically or in response to a user input. The region of interest 314 may be modifiable by user input received via the user input device 130 and/or touchscreen display 130, 134 to adjust a position and/or size of the region of interest 314. The region of interest 314 may be provided by the region of interest processor 150 to the graphical marker processor 160.

Figure 3:
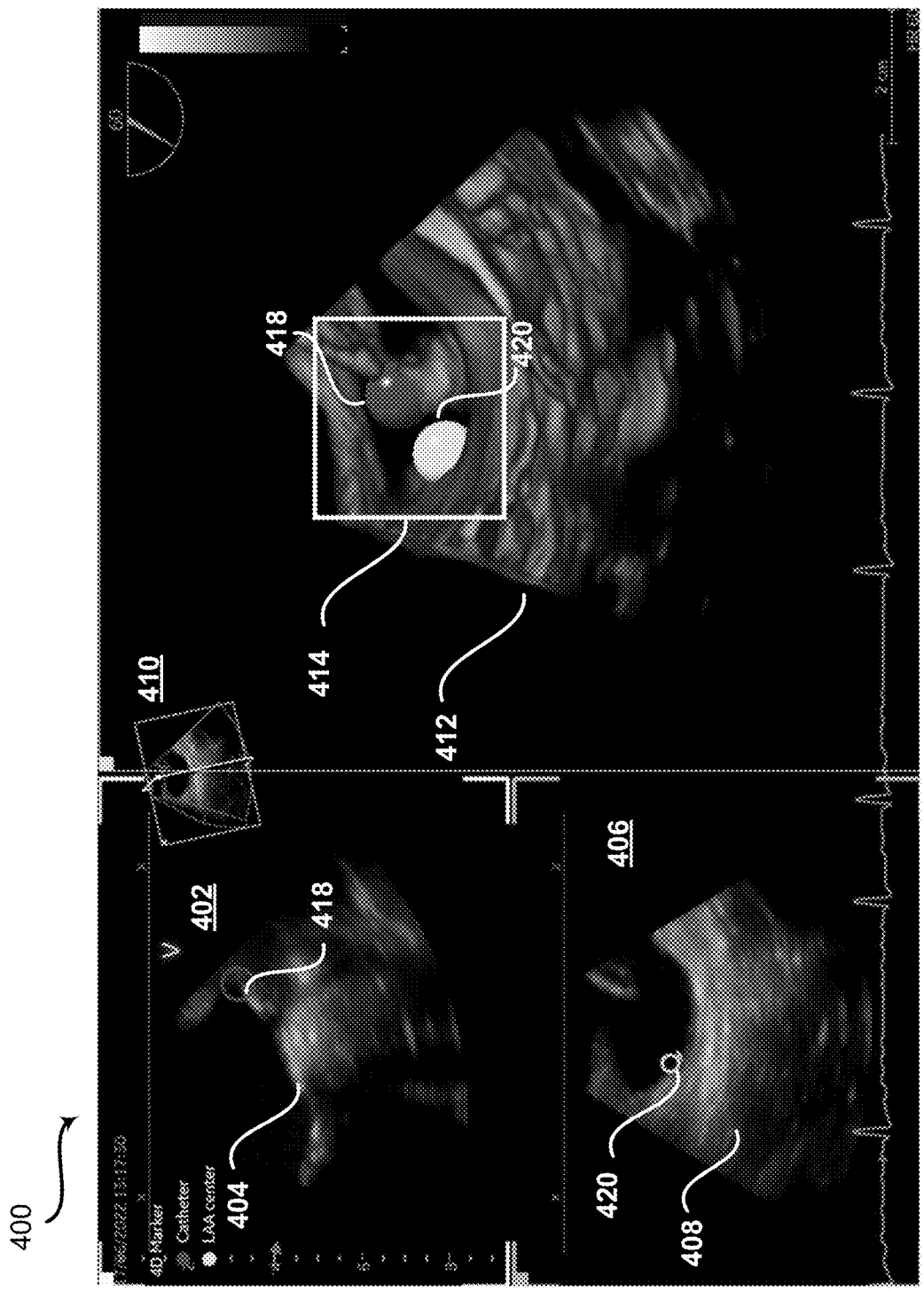
FIG. 3 is a second exemplary display 400 of two-dimensional (2D) ultrasound images and a 3D/4D ultrasound image of an anatomical structure before placement of a medical device, in accordance with various embodiments.

FIG. 3 is a second exemplary display 400 of two 2D ultrasound images 404, 408 and a 3D/4D ultrasound image 412 of an anatomical structure during placement of a medical device, in accordance with various embodiments. Referring to FIG. 3, the display 400 comprises a first image display portion 402 comprising a 2D ultrasound image 404, and a second image display portion 406 comprising a second 2D ultrasound image 408. A detected and localized target region of interest 414 may also be provided on a main display 410 of the display system 134 with the image display portions 402, 406 as shown in FIG. 3 and/or may be provided on a touch panel of the display system 134. A graphical marker 418 and a graphical marker 420 may be overlaid on the 2D ultrasound images 404, 408, and/or on the 3D/4D ultrasound image 412.

A user input device 130 may be used to initiate the acquisition of the 2D ultrasound images 404, 408, and/or the 3D/4D ultrasound image 412, or the 2D ultrasound images 404, 408, and the 3D/4D ultrasound image 412 may be obtained automatically. The 2D images 404, 408 may additionally and/or alternatively be a single 2D image, a rendering of a volume (3D/4D), 2D image slices extracted from a volume (3D/4D), and/or any suitable ultrasound images. Although the 2D images 404, 408 and the 3D/4D image 412 are depicted in various positions on the display, the positions of the 2D ultrasound images 404, 408 and the 3D/4D image 412 may be customized and displayed in different positions on the display 400.

The graphical marker 418 may be used to indicate a current location in space and time of a catheter that will be used to place a medical device at a target placement location within the region of interest 414. The graphical marker 420 may be used to indicate the target placement location in space and time of a medical device within the region of interest. The graphical marker 420 indicating the target placement location of the medical device may be obtained automatically using the structure detection processor 140 and/or the region of interest processor 150, or may be input by a user to visually indicate a location within the region of interest 414. If the target placement location is obtained automatically, the target placement location may be modified via user input. The 3D/4D ultrasound 412 may be overlaid with the graphical marker 418 and the graphical marker 420 to indicate a proximity between the graphical marker 418 and the graphical marker 420 to an operator. Additionally or alternatively, the target placement location may be provided by the graphical marker processor 160 to the locking processor 190.

Referring to FIG. 1, the graphical marker processor 160 may comprise suitable logic, circuitry, interfaces and/or code that may be configured to overlay graphical markers on, within, or near a target structure or region of interest in response to a user input or automatically based on the information provided by the structure detection processor 140 and/or the region of interest processor 150. For example, the graphical marker processor 160 may place a graphical marker 418 on 2D ultrasound image 404, and a graphical marker 420 on 2D ultrasound image 408. The graphical marker 418 may be used to identify a first location corresponding to a location in space and time of a catheter that will be used place the medical device at the target location. The graphical marker processor 160 may overlay the 2D ultrasound image 404 and/or the 3D/4D image 412 with the graphical marker 418 to indicate the current location of the catheter. The graphical marker processor 160 may place a graphical marker 420 on the 2D ultrasound image 408. The graphical marker processor 160 may overlay the 2D ultrasound image 408 and/or the 3D/4D image 412 with the graphical marker 420 in order to identify a second location representing a target placement location in space and time of the medical device. The graphical marker processor 160 may place both the first marker 418 and the second marker 420 on the 3D/4D image 412 to provide real-time location information for the target placement location and the catheter. The graphical marker processor 160 may provide a circular visual indicator as depicted in FIG. 3 (see graphical marker 418 and graphical marker 420), provide a different shape of visual indicator, colorize pixels, provide different graphical effects (e.g., blinking, flashing, pulsing, color-changing, etc.), as non-limiting examples and may be customizable by a user. The graphical marker processor may also output alerts, such as sound, visual indicators, textual indicators, and may change visual indications based on proximity from the first marker 418 to the second marker 420, or based on a proximity from the first marker 418 and/or the second marker to additional markers and/or to regions of interest 414.

Although two graphical markers are depicted in FIG. 3, additional graphical markers may be included in the 2D ultrasound images 404, 408 and/or the 3D/4D image 412. The graphical marker processor 160 may receive information from the structure tracking processor 170 and the catheter tracking processor 180 in order to update the placement of the graphical marker 418 and the graphical marker 420 on the 2D ultrasound images 404, 408, and/or on the 3D/4D image 412, respectively.

Figure 4:
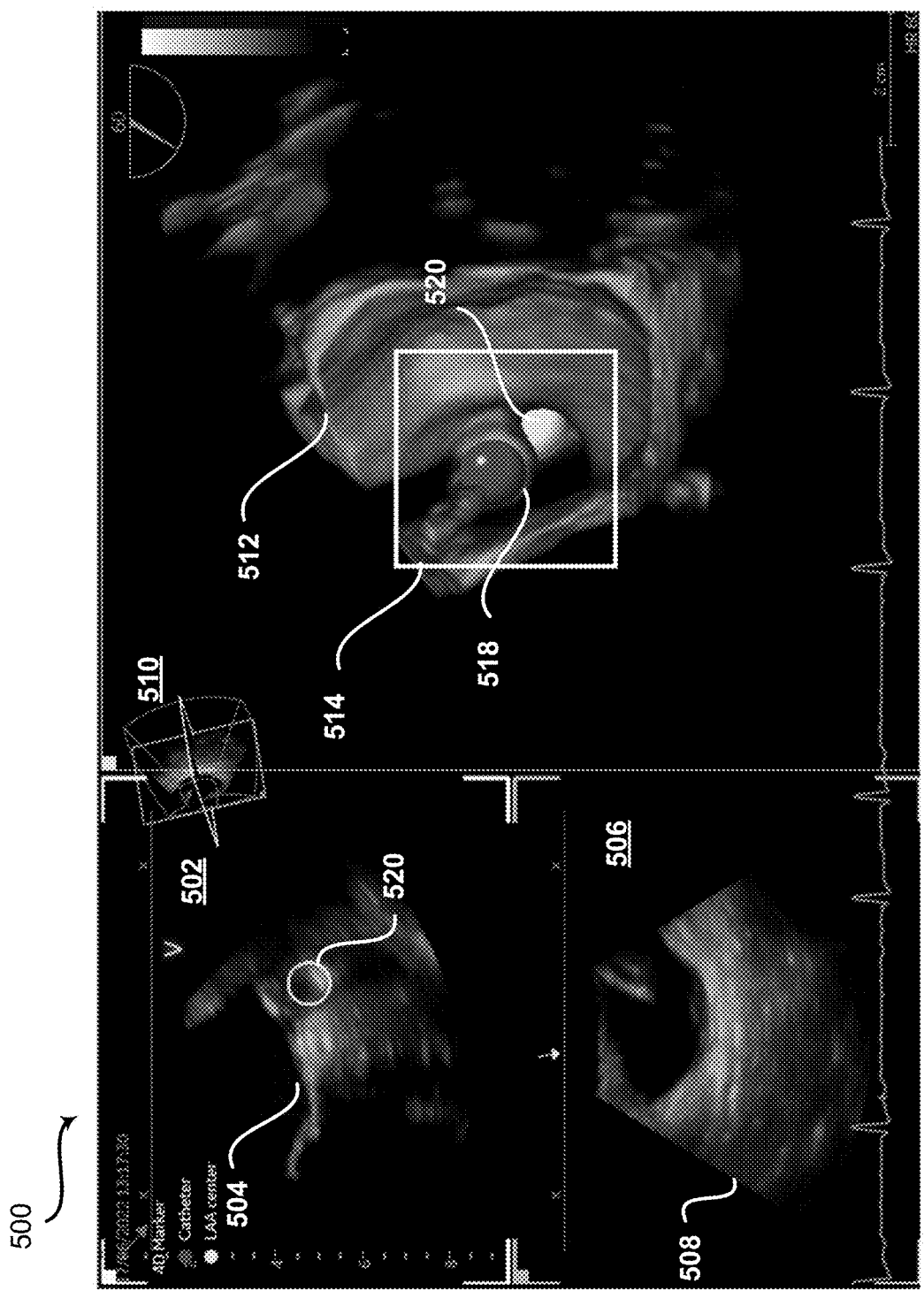
FIG. 4 is a third exemplary display 500 of two-dimensional (2D) ultrasound images and a 3D/4D ultrasound image of an anatomical structure before placement of a medical device, in accordance with various embodiments.

FIG. 4 is a third exemplary display 500 of two 2D ultrasound images and a 3D/4D ultrasound image of an anatomical structure during placement of a medical device, in accordance with various embodiments. Referring to FIG. 4, the display 500 comprises a first image display portion 502 comprising a 2D ultrasound image 504, and a second image display portion 506 comprising a second 2D ultrasound image 508. A detected and localized target region of interest 514 may also be provided on a main display of the display system 134 with the first image display portion 502 and second image display portion 506 as shown in FIG. 4 and/or may be provided on a touch panel of the display system 134. A graphical marker 518 and a graphical marker 520 may be overlaid on the 2D ultrasound images 504, 508, and/or on a region of interest 514 of the 3D/4D ultrasound image 512. The 3D/4D ultrasound may be overlaid with the graphical marker 518 and the graphical marker 520 to indicate a location of the graphical marker 518 and the second graphical marker and/or a proximity between the graphical marker 518 and the graphical marker 520 to an operator.

Similar to FIG. 3, a user input device 130 may be used to initiate the acquisition of the 2D ultrasound images 504, 508, and/or the 3D/4D ultrasound image 512, or the ultrasound images may be obtained automatically, and each of the ultrasound images 504, 508, 512 may be placed in different arrangements on the display 500. The 2D images 404, 408 may additionally and/or alternatively be a single 2D image, a rendering of a volume (3D/4D), 2D image slices extracted from a volume (3D/4D), and/or any suitable ultrasound images.

Figure 5:
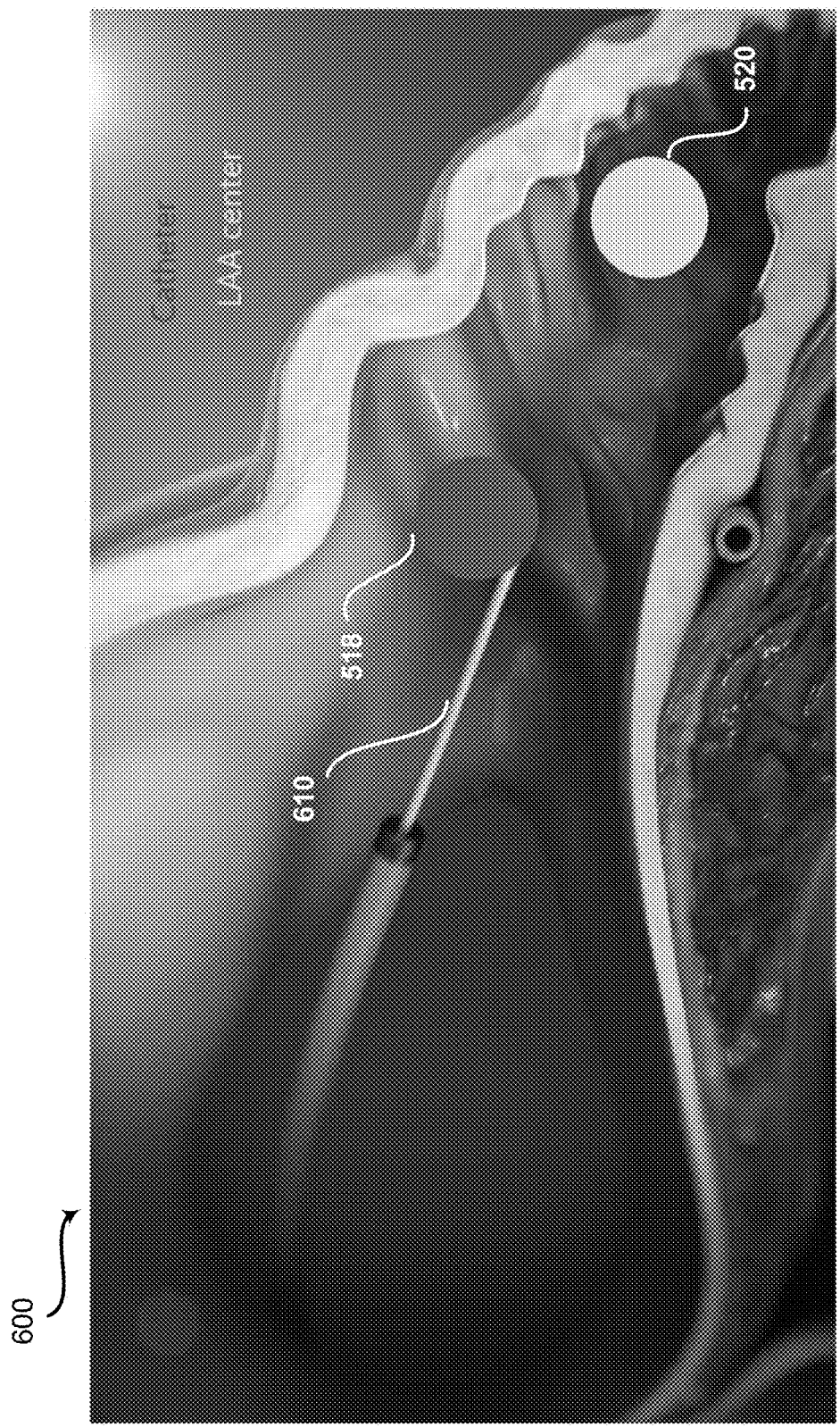
FIG. 5 is a graphical representation 600 including markers before placement of a medical device in an anatomical structure, in accordance with various embodiments.

FIG. 5 is a graphical representation 600 before placement of a medical device in an anatomical structure, in accordance with various embodiments. Referring to FIG. 5, a graphical marker 518 indicates a location corresponding to a location in space and time of the catheter 610, and a graphical marker 520 designates a location representing a target placement location in space and time of a catheter 610 in accordance with various embodiments. As the catheter 610 (indicated by the graphical marker 518) moves toward the target placement location indicated by the graphical marker 520, the location of the catheter 610 (e.g., the graphical marker 518) is tracked. The target placement location indicated by the graphical marker 520 may be tracked in space and time by the structure tracking processor 170, and the location indicated by the graphical marker 518 and representing the location of the catheter 610 may be tracked in space and time by the catheter tracking processor 180.

Referring to FIG. 1, the structure tracking processor 170 comprises suitable logic, circuitry, interfaces, and/or code that may be operable to track the target structure and/or region of interest surrounding the target placement location of the medical device The catheter tracking processor 180 comprises suitable logic, circuitry, interfaces, and/or code that may be operable to track a location corresponding to the space and time of the catheter. For example, as the catheter (represented by the graphical marker 518) is guided towards the target location for placement of the medical device (represented by the graphical marker 520), the catheter tracking processor tracks the location of the catheter, and the structure tracking processor tracks the target placement location.

The structure tracking processor 170 may track the second location (e.g., indicated by graphical marker 520 in FIG. 5) and the catheter tracking processor 180 may track the first location (e.g., indicated by graphical marker 518 in FIG. 5) of the catheter by using artificial intelligence and/or machine learning. In some examples, the structure tracking processor 170 and the catheter tracking processor 180 may track the second location and the first location, respectively, by performing atlas segmentation. Atlas segmentation involves the use of atlases, which are labeled maps of anatomical structures (e.g., left atrial appendage (LAA) and/or LAA structures, mitral valve, gastroenterological structures, urological structures, reproductive structures, cardiac structures, pulmonary structures, and/or any suitable anatomical structures). The atlases may be created by capturing ultrasound images of anatomical structures and then manually segmenting the ultrasound images. The atlases may then be employed to segment new, unseen images using a process called registration (e.g., template matching). For example, the structure tracking processor 170 may transform and deform an acquired ultrasound image so that the structures on the acquired ultrasound image align with the corresponding structures in a manually segmented ultrasound image in the atlases. Mathematical scoring functions may be utilized to assess how well one image aligns with the other, which aides in localizing and tracking anatomical structures and allowing the structure tracking processor 170 to track the target placement location within a region of interest in space and time. The structure tracking processor 170 may provide the target placement location to the graphical marker processor 160 so that the graphical marker processor 160 may update the graphical marker 520. The structure tracking processor 170 may also provide the target placement location to the locking processor 190. Similarly, the catheter tracking processor 180 may use registration to determine a current location of the catheter in space and time and provide the current location to the graphical marker processor 160 to update the graphical marker 518 and/or to the locking processor 190.

Additionally or alternatively, the structure tracking processor 170 may track the second location by using a machine learning approach. In some examples, the machine learning method uses segmentation masks to produce a mask reconstruction network, original images to produce a segmentation network, and latent space alignment which performs feature alignment between the original images and the segmentation network with constant learning loss to enhance the feature alignment. The mask reconstruction network may be based on a ConvNext model to obtain latent space features of the masks. The LAA segmentation network may be constructed using a U-shape structure which consists of an encoder, a decoder, and skip connection layers. The encoder enables the extraction of shallow and deep features of the fused image to obtain the latent space, after which the decoder is utilized to recover the mask prediction results from the latent space. The skip connection layers fuse the feature map at each stage of the encoder with the feature map obtained by upsampling the decoder layers, thereby allowing the decoder to access high-level features learned by the encoder and helps the decoder to accurately preserve the details of the input image. Generative adversarial learning (GAN) may be used to align the segmentation network's latent space with the mask reconstruction network's latent space vector, thus introducing prior knowledge of the LAA mask. A latent space alignment loss combining adversarial-based loss and contrast learning loss aligns the latent space of the reconstructed network with that of the segmentation network. The contrast learning loss may be used to enhance the association between the prior latent features and the latent space features of the original image to increase the LAA segmentation accuracy. In this way, the structure tracking processor 170 may use an acquired ultrasound image to determine the location in space and time of a target placement location within a region of interest within or near an anatomical structure. The structure tracking processor 170 may provide the location of the target placement location within the region of interest and/or structure to the graphical marker processor 160 and/or to the locking processor 190. Although the GAN model above is described with respect to the LAA, the GAN model may utilize other structures such as a mitral valve, gastroenterological structures, urological structures, reproductive structures, cardiac structures, pulmonary structures, and/or any suitable anatomical structures.

The structure tracking processor 170 and the catheter tracking processor 180 may each use different artificial intelligence and/or machine learning approaches, both may use the same approach(es), a combination of approaches, or approaches similar to those described above. The structure tracking processor 170 and the catheter tracking processor 180 may provide the first location and/or the second location to the graphical marker processor 160 and/or the locking processor 190 and may additionally, or alternatively, provide the first location and/or the second location to the archive 138 and/or any suitable computer readable medium.

Figure 6:
FIG. 6 is an exemplary display 700 of 2D ultrasound images and a 3D/4D ultrasound image during placement of a medical device in an anatomical structure, in accordance with various embodiments.

FIG. 6 is an exemplary display 700 of two 2D ultrasound images and a 3D/4D ultrasound image of an anatomical structure during placement of a medical device, in accordance with various embodiments. The display 700 comprises a first image display portion 702 comprising a 2D ultrasound image 704, and a second image display portion 706 comprising a second 2D ultrasound image 708. A detected and localized region of interest 714 may also be provided on a main display of the display system 134 with the first image display portion 702 and second image display portion 706 as shown in FIG. 4 and/or may be provided on a touch panel of the display system 134. A combined graphical marker 730 may be overlaid on the 2D ultrasound images 704, 708, and/or on a region of interest 714 of the 3D/4D ultrasound image 708. The combined graphical marker 730 may be overlaid on the display by the graphical marker processor 160 and may indicate that two graphical markers (e.g., 518, 520 of FIG. 4, for example) are overlapping (e.g., that a first graphical marker has reached a second graphical marker).

Referring to FIG. 1, a locking processor 190 comprises suitable logic, circuitry, interfaces, and/or code that may be operable to provide a locking mechanism that designates the target placement location of a medical device and guides the catheter to the target placement location. The locking processor 190 may be configured to receive current location information (e.g., location in space and time of the target placement location within a region of interest and/or a structure and location in space and time of a catheter) from the structure tracking processor 170 and catheter tracking processor 180, respectively. The locking processor 190 may use a locking mechanism to define the target placement location within the region of interest using the location information received from the structure tracking processor. The locking processor may then use the current location in space and time of the catheter obtained from the catheter tracking processor 180, to determine the proximity of the catheter to the target placement location (e.g., the target for the locking mechanism), and when the catheter reaches the target placement location, the locking processor 190 may send an output signal. In some examples, the output signal is a signal to automatically release the catheter into the target placement location within the region of interest and/or the structure. In some examples, the output signal may be a notification, such as a visual (e.g., an alert on the display system 134), auditory (e.g. a sound), and/or physical indicator (e.g. vibration of ultrasound probe) so that an operator may release the catheter in order to place the medical device in the target placement location.

Figure 7:
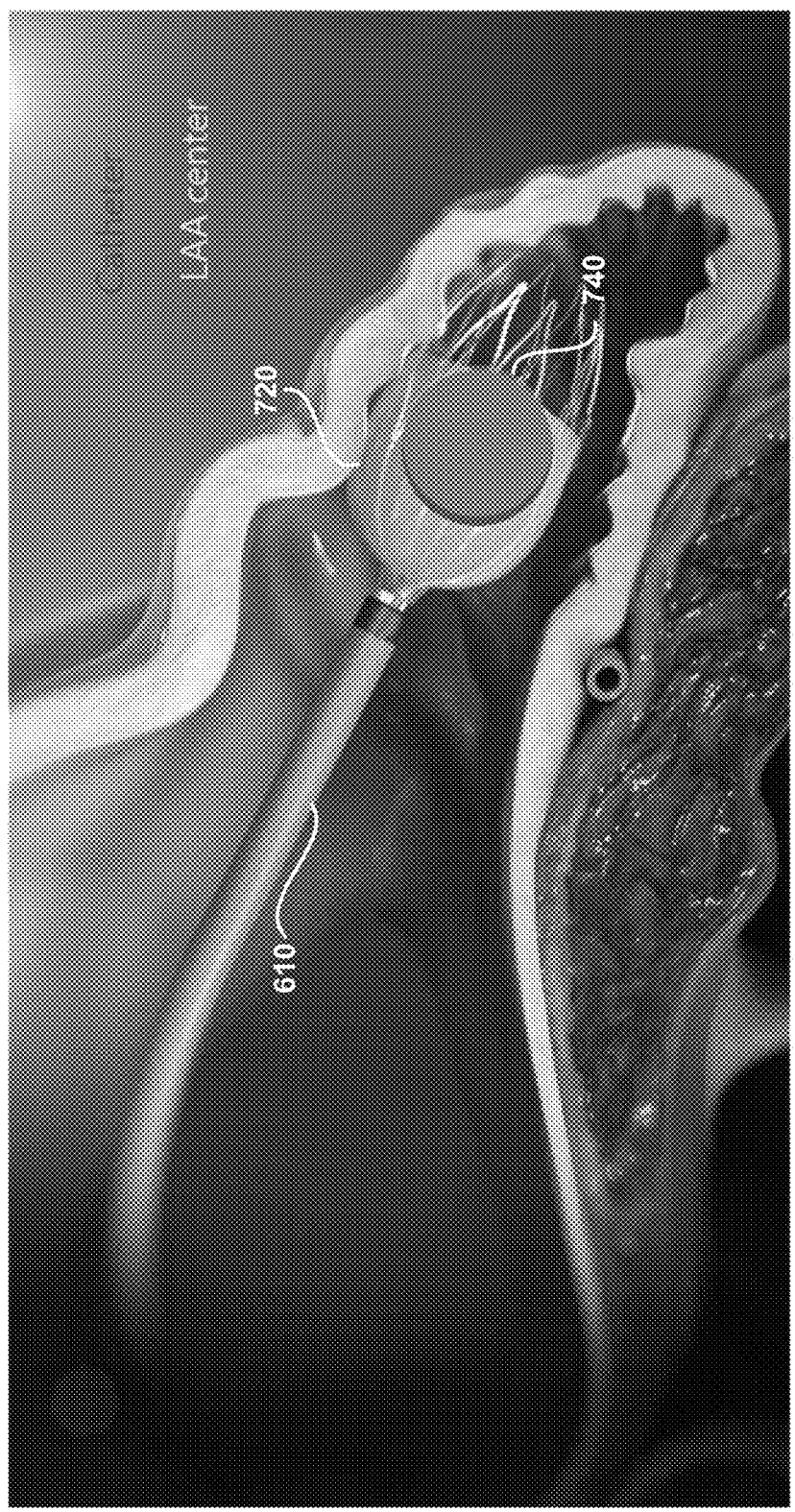
FIG. 7 is a graphical representation 800 during placement of a medical device in an anatomical structure, in accordance with various embodiments.

FIG. 7 is a graphical representation 800 during placement of a medical device in an anatomical structure, in accordance with various embodiments. Referring to FIG. 7, the graphical representation 800 includes a catheter 610, a medical device 720, and an overlapping graphical marker 740 during placement of a medical device in an anatomical structure, in accordance with various embodiments. As the catheter 610 moves toward the target placement location, the location of the catheter 610 is tracked by the catheter tracking processor 180. The target placement location is also tracked in space and time by the structure tracking processor 170. The locking processor 190 may obtain the current target placement location from the structure tracking processor 170 and the catheter location from the catheter tracking processor 180. The locking processor 190 may track the current location of the catheter as the catheter moves towards the target placement location. Once the catheter 610 reaches the target placement location (indicated by overlapping graphical marker 740 in FIG. 7), the locking processor 190 determines that the location of the catheter matches the target placement location of the medical device 720 and may output a signal indicating the match. Additionally, or alternatively, the graphical marker processor 160 may determine that the first marker 518 and the second marker 520 are overlapping. Once the determination is made, an output signal is sent by the locking processor. The output signal may be a signal to automatically release the medical device 720 into the target placement location within the structure. In some examples, the output signal may be a notification, such as a visual or auditory indicator so that an operator may manually release the catheter to be placed in the target location.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present 2D ultrasound images 304, 308, 404, 408, 504, 508, 704, 708, 804, 806, rendered 3D/4D volumes 312, 412, 512, 712, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores 2D ultrasound images 304, 308, 404, 408, 504, 508, 704, 708, 804, 806, rendered 3D/4D volumes 312, 412, 512, 712, instructions for automatically detecting and tracking target structures and other anatomical structures, instructions for causing a display system 134 to present regions of interest 314, 414, 514, 714 within or near target structures and other anatomical structures, instructions for triggering additional ultrasound image acquisitions (e.g., 3D/4D volume acquisition), instructions for identifying and tracking a target placement location of a medical device within a region of interest, instructions for identifying and tracking a catheter within anatomical structures, instructions for overlaying ultrasound image acquisitions with graphical markers and dynamically updating the graphical markers on the ultrasound image acquisitions over time, instructions for outputting a signal when the graphical markers overlap and/or when the location of the catheter and target placement location match, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 210 may comprise suitable logic, circuitry, interfaces and/or code that may be operable to train the neurons of the deep neural network(s) (e.g., artificial intelligence model(s)) inferenced (i.e., deployed) by the structure detection processor 140, the region of interest processor 150, graphical marker processor 160, structure tracking processor 170, and/or catheter tracking processor 180. For example, the artificial intelligence model inferenced by the structure detection processor 140 may be trained to automatically identify anatomical structures depicted in an ultrasound image and/or volume using database(s) 220 of classified ultrasound images and/or volumes of anatomical structures. As another example, the artificial intelligence model inferenced by the structured detection processor 140 and/or region of interest processor 150 may be trained to automatically identify target structures, surrounding structures, target structure shapes, major/minor axes of target structures, and the like depicted in an ultrasound volume using database(s) 220 of classified ultrasound volumes of possible target structures.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms. In some examples, the training image databases may include atlases (e.g., labeled maps of anatomical structures, original images, segmentation masks, as non-limiting examples).

Figure 8:
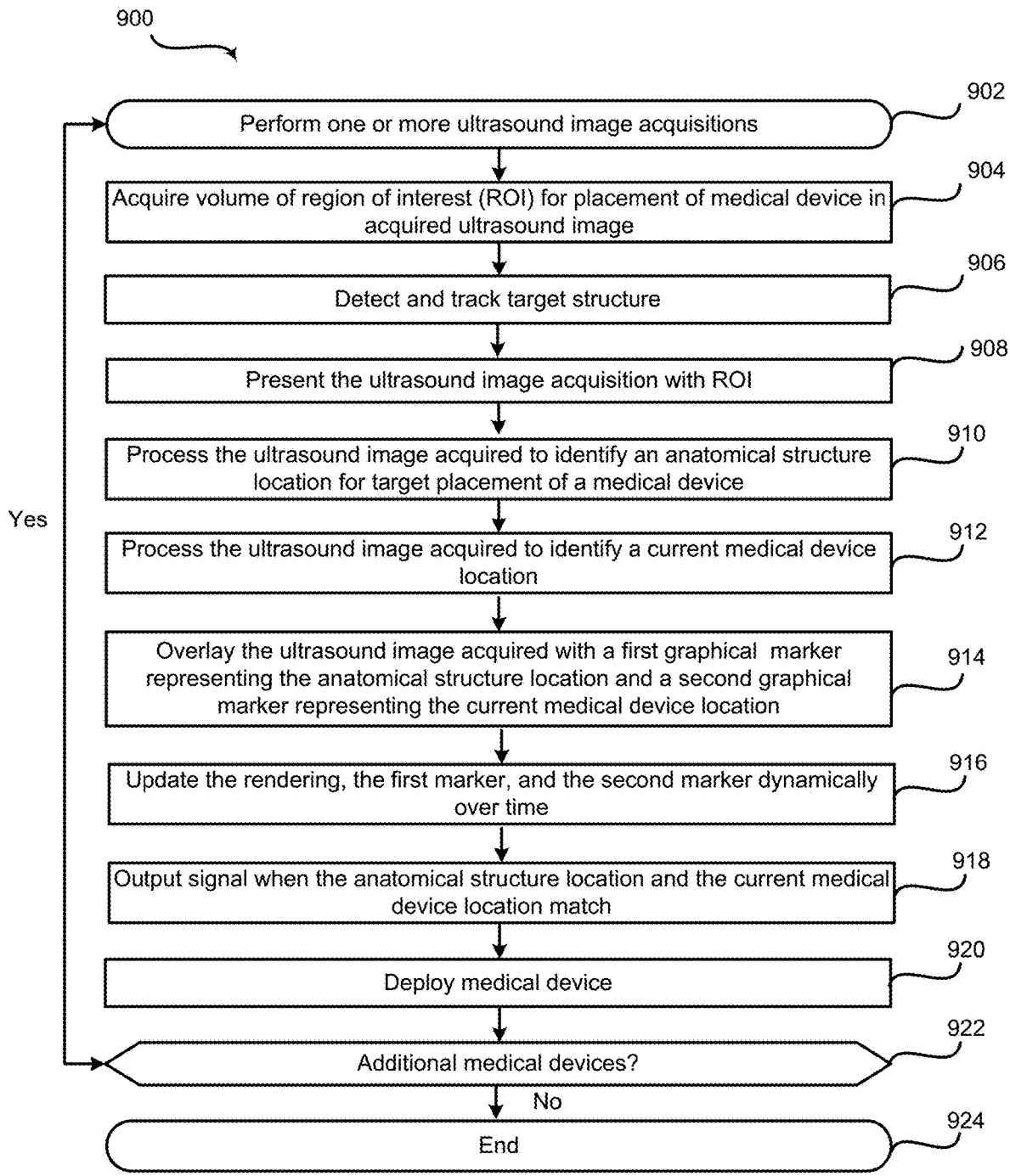
FIG. 8 is a flow chart 900 illustrating exemplary steps that may be utilized for automatically placing a medical device in an anatomical structure using a locking mechanism, in accordance with various embodiments.

FIG. 8 is a flow chart 900 illustrating exemplary steps 902-922 that may be utilized for automatically placing a medical device in an anatomical structure using a locking mechanism, in accordance with various embodiments. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 902, a signal processor 132 of the ultrasound system 100 may be configured to receive a user input selecting a target structure 312. For example, a structure detection processor 140 may be configured to receive a user input selecting a target structure 312, such as a left atrial appendage (LAA), a mitral valve, a gastroenterological structure, a urological structure, a reproductive structure, a cardiac structure, a pulmonary structure, and/or any suitable anatomical structures, as non-limiting examples, via a user input device 130. The structure detection processor 140 may initiate an initial ultrasound image acquisition in response to the selection of a target structure 312.

At step 904, an ultrasound probe 104 of an ultrasound system 100 performs an initial ultrasound image acquisition. For example, the ultrasound probe 104 may be operable to acquire 2D ultrasound images 304, 308, 404, 408, 504, 508, 704, 708, 3D/4D volumes 312, 412, 512, 712, and/or any suitable ultrasound images. The acquired ultrasound images 304, 308, 404, 408, 504, 508, 704, 708 and/or volumes 312, 412, 512, 712, of the initial ultrasound image acquisition may be provided to the structure detection processor 140 and/or stored at archive 138 and/or any suitable computer readable medium.

At step 906, the signal processor 132 of the ultrasound system 100 automatically detects and tracks the target structure 312 in the initial ultrasound image acquisition. For example, the structure detection processor 140 may be configured to analyze acquired ultrasound images 304, 308, 404, 408, 504, 508, 704, 708 and/or volumes to detect a presence and location of the selected target structure 312 in the ultrasound images 304, 308, 404, 408, 504, 508, 704, 708 and/or volumes 312, 412, 512, 712. The structure detection processor 140 may include, for example, image analysis algorithms, one or more deep neural networks (e.g., a convolutional neural network such as u-net) and/or may utilize any suitable form of image analysis techniques, artificial intelligence, or machine learning processing functionality configured to detect and localize anatomical structures in ultrasound images and/or volumes. The detected and localized target structure 312 may be provided by the structure detection processor 140 to the region of interest processor 150. Additionally and/or alternatively, the detected and localized target structure 312 may be stored at archive 138 and/or any suitable computer readable medium.

At step 908, the signal processor 132 of the ultrasound system 100 presents the initial ultrasound image acquisition 304, 308, 404, 408, 504, 508, 704, 708 with a region of interest 314, 414, 514, 714 within, or proximate to, the target structure 312, 412, 512, 712 at a display system 134. For example, a region of interest processor 150 of the signal processor 132 may be configured to cause a display system 134 to present the initial ultrasound image acquisition 304, 308 with a region of interest 408 within or near a selected target structure 312 detected and localized by the structure detection processor 140. The region of interest processor 150 may be configured to receive from the structure detection processor 140, or retrieve from the archive 138 and/or any suitable data storage medium, the identity and location of a selected target structure 312. The region of interest processor 150 may be configured to identify the localized selected target structure by overlaying a marker, a bounding box, colorizing pixels, and/or any suitable identification technique. The region of interest 314, 414, 514, 714 may be automatically detected or may be input by the user.

At step 910, the signal processor 13 of the ultrasound system 100 may process the ultrasound image acquired to identify an anatomical structure location, which is a target placement location for a medical device in the region of interest. For example, a graphical marker processor 160 may be configured to indicate the anatomical structure location on a display using a graphical marker 420, 520. The anatomical structure location may be determined automatically by the graphical marker processor 160 using information obtained from the region of interest processor 150 or may be input by the user. The graphical marker processor 160 may provide the anatomical structure location to the structure tracking processor 170 and/or the locking processor and may provide real-time updates of the anatomical structure location at the display system 134.

At step 912, the signal processor may process the second ultrasound image acquired to identify a current medical device location corresponding to a current location of the medical device to be placed in the anatomical structure location. For example, a graphical marker processor 160 may be configured to indicate the current medical device location on a display using a graphical marker 418, 518. The current medical device location may be determined automatically by the graphical marker processor 160 using information obtained from the region of interest processor 150 and/or the structure processor. The graphical marker processor 160 may provide the current medical device location to the catheter tracking processor 180 and/or the locking processor 190 and may provide real-time updates of the current medical device location at the display system 134.

At step 914, the signal processor may process the first and second ultrasound images to overlay the ultrasound images acquired with a first graphical marker representing the anatomical structure location and/or a second graphical marker representing the current medical device location. The graphical marker processor 160 may provide the anatomical structure location and the current medical device location to the structure tracking processor 170 and the catheter tracking processor 180, respectively, and may provide real-time updates of the anatomical structure location at the display system 134. The 3D/4D ultrasound 412, 512, 712 may be overlaid with the graphical marker 418, 518 and the graphical marker 420, 520. Additionally or alternatively, the anatomical structure location and/or the current medical device location may be provided by the graphical marker processor 160 and/or to the locking processor 190.

At step 916, the signal processor tracks the structure, along with the anatomical structure location over time and updates the overlaid ultrasound images. For example, the structure tracking processor 170 and the catheter tracking processor 180 may obtain the anatomical structure location and the current medical device location, respectively, and may provide real-time updates of the anatomical structure location and the current medical device location to the graphical marker processor 160. The 3D/4D ultrasound 412, 512, 712 with the overlaid graphical markers 418, 518, 420, 520. Additionally or alternatively, the structure tracking processor 170 and the catheter tracking processor 180 may provide real-time updates of the anatomical structure location and/or the current medical device location to the graphical marker processor 160 to update the display system 134 dynamically over time and/or to the locking processor 190.

At step 918, the signal processor tracks the anatomical structure location and the current medical device location in space and time, and when the anatomical structure location and the current medical device location match, the signal processor outputs a signal. For example, the structure tracking processor 170 and the catheter tracking processor 180 may provide real-time updates of the anatomical structure location and/or the current medical device location to the locking processor 190, and when the locking processor 190 detects a match, the locking processor 190 may output a signal. In some examples, the output signal is a signal to automatically release the catheter into the target placement location within the region of interest and/or the structure. In some examples, the output signal may be a notification, such as a visual (e.g., an alert on the display system 134), auditory (e.g. a sound), and/or physical indicator (e.g. vibration of ultrasound probe) so that an operator may release the catheter in order to place the medical device in the anatomical structure location (i.e., target placement location).

At step 920, the output signal is used to deploy the medical device. In some examples, the output signal is a signal to automatically release the catheter into the target placement location within the region of interest and/or the structure. In some examples, the output signal may be a notification, such as a visual (e.g., an alert on the display system 134), auditory (e.g. a sound), and/or physical indicator (e.g. vibration of ultrasound probe) so that an operator may release the catheter in order to place the medical device in the target placement location At step 922, the signal processor determines whether additional medical devices will be deployed. If there are additional medical devices to be placed in or around an anatomical structure, the method will begin again at step 902. In some examples, a medical device such a watchman device may be placed, and a mitral valve clip may subsequently be placed. In some other examples, a mitral valve clip is placed and then a watchman device is placed. In some examples, one or more medical devices, such as gastroenterology devices, urology devices, cardiac devices, pulmonary devices, reproductive devices, etc. may be placed using via the process 900, and an additional medical device may be placed at step 922 by repeating the process 900. If there are no additional medical devices to be placed in or around an anatomical structure, the process 900 ends at step 924.

Aspects of the present disclosure provide a method 900 and system 100 for placement of a medical device 720 in an anatomical structure comprising performing 902, by an ultrasound probe 104 of an ultrasound system 100, one or more ultrasound image acquisitions 304, 308, 404, 408, 312, 412, 504, 508, 512, 704, 708, 712. The method 900 may comprise detecting and tracking, by at least one processor 132, 140, 150, 170 of the ultrasound system, one or more anatomical structures in the one or more ultrasound image acquisitions 304, 308, 404, 408, 312, 412, 504, 508, 512, 704, 708, 712. The method 900 may comprise causing 908, by the at least one processor 132, 140, 150, a display system to present a volume 412, 512, 712 of a region of interest 314 414 514 714 within or surrounding the one or more anatomical structures in the one or more ultrasound image acquisitions 304, 308, 404, 408, 312, 412, 504, 508, 512, 704, 708, 712. The method 900 may comprise processing 910, by the at least one processor 132, 140, 170, the one or more ultrasound image acquisitions 304, 308, 404, 408, 312, 412, 504, 508, 512, 704, 708, 712 to identify a first location corresponding to a target placement location within the region of interest 314 414 514 714 for a medical device 720. The method 900 may comprise processing 912, by the at least one processor 132, 180, the one or more ultrasound image acquisitions 304, 308, 404, 408, 312, 412, 504, 508, 512, 704, 708, 712 to identify a second location corresponding to a location of a catheter 610 including the medical device 720. The method 900 may comprise outputting a signal 916, by the at least one processor 132, 170, 180, 190, to deploy 920 the medical device 720 when the second location corresponding to the location of the catheter 610 matches the first location corresponding to the target placement location 420, 520 for the medical device 720.

In an exemplary embodiment, the method 900 comprises rendering 914, by the at least one processor 132, 140, 150, 160 the one or more ultrasound image acquisitions 304, 308, 404, 408, 312, 412, 504, 508, 512, 704, 708, 712 overlaid with a first graphical marker 418, 518 corresponding to the first location and a second graphical marker 420, 520 corresponding to the second location. In a representative embodiment, the method 900 further comprises updating 916, by the at least one processor 132, 160 the first graphical marker 418, 518 corresponding to the target placement location as the first location is tracked by the at least one processor 132, 170 and updating 916 the second graphical marker 420, 520 corresponding to the catheter 610 as the second location is tracked by the at least one processor 132, 180. In various embodiments, the method 900 comprises the matching of the first location and the second location is indicated by the first graphical marker 418, 518 overlapping 730, 740 with the second graphical marker 420, 520. In some example embodiments, the method 900 comprises automatically deploying the medical device 720 when the signal is output. In an exemplary embodiment, the method 900 comprises transmitting a notification to an operator to deploy the medical device 720 when the signal is output. In an exemplary embodiment, the one or more anatomical structures is a left atrial appendage (LAA).

Various embodiments provide an ultrasound system 100 comprising an ultrasound probe 104 configured to perform one or more ultrasound image acquisitions 304, 308, 404, 408, 312, 412, 504, 508, 512, 704, 708, 712, at least one processor 132, 140, 170 configured to detect and track one or more anatomical structures in the one or more ultrasound image acquisitions 304, 308, 404, 408, 312, 412, 504, 508, 512, 704, 708, 712. The at least one processor may be configured to cause a display system to present a volume of a region of interest 314 414 514 714 within or surrounding the one or more anatomical structures in the one or more ultrasound image acquisitions 304, 308, 404, 408, 312, 412, 504, 508, 512, 704, 708, 712. The at least one processor may be configured to process the one or more ultrasound image acquisitions 304, 308, 404, 408, 312, 412, 504, 508, 512, 704, 708, 712 to identify a first location corresponding to a target placement location within the region of interest 314 414 514 714 for a medical device 720. The at least one processor may be configured to process the one or more ultrasound image acquisitions 304, 308, 404, 408, 312, 412, 504, 508, 512, 704, 708, 712 to identify a second location corresponding to a location of a catheter 610 including the medical device 720. The at least one processor may be configured to output a signal to deploy the medical device 720 when the second location corresponding to the location of the catheter 610 matches the first location corresponding to the target placement location for the medical device 720.

In a representative embodiment, the at least one processor is configured to render the one or more ultrasound image acquisitions 304, 308, 404, 408, 312, 412, 504, 508, 512,

704, 708, 712 overlaid with a first graphical marker 418, 518 corresponding to the first location and a second graphical marker 420, 520 corresponding to the second location. In various embodiments, the at least one processor 132, 160 further configured to update the first graphical marker 418, 518 corresponding to the target placement location as the first location is tracked by the at least one processor 132, 170 and updating the second graphical marker 420, 520 corresponding to the catheter 610 as the second location is tracked by the at least one processor 132, 180. In certain embodiments, the at least one processor is further configured to match the first location and the second location is indicated by the first graphical marker 418, 518 overlapping with the second graphical marker 420, 520. In various embodiments, the at least one processor further configured to automatically deploy the medical device 720 when the signal is output. In certain embodiments, the at least one processor 132, 190 further configured to transmit a notification to an operator to deploy the medical device 720 when the signal is output. In a representative embodiment, the one or more anatomical structures is a left atrial appendage (LAA).

Various embodiments provide an ultrasound system 100 for medical device 720 placement in an anatomical structure comprising an ultrasound probe 104 configured to perform one or more ultrasound image acquisitions 304, 308, 404, 408, 312, 412, 504, 508, 512, 704, 708, 712. The at least one processor 132, may be configured to detect and track a left atrial appendage (LAA) in the one or more ultrasound image acquisitions 304, 308, 404, 408, 312, 412, 504, 508, 512, 704, 708, 712. The at least one processor may be configured to cause a display system to present a volume of a region of interest 314 414 514 714 within or surrounding the LAA in the one or more ultrasound image acquisitions 304, 308, 404, 408, 312, 412, 504, 508, 512, 704, 708, 712. The at least one processor may be configured to process the one or more ultrasound image acquisitions 304, 308, 404, 408, 312, 412, 504, 508, 512, 704, 708, 712 to identify a first location corresponding to a target placement location within the region of interest 314 414 514 714 for a medical device 720. The at least one processor may be configured to process the one or more ultrasound image acquisitions 304, 308, 404, 408, 312, 412, 504, 508, 512, 704, 708, 712 to identify a second location corresponding to a location of a catheter 610 including the medical device 720. The at least one processor 132, 140, 150, 160 may be configured to render the one or more ultrasound image acquisitions 304, 308, 404, 408, 312, 412, 504, 508, 512, 704, 708, 712 with an indication of the first location and an indication of the second location. The at least one processor 132, 190 may be configured to output a signal to automatically deploy the medical device 720 when the second location corresponding to the location of the catheter 610 matches the first location corresponding to the target placement location for the medical device 720.

In a representative embodiment, the at least one processor 132, 160 may be further configured to overlay the one or more ultrasound image acquisitions 304, 308, 404, 408, 312, 412, 504, 508, 512, 704, 708, 712 with a first graphical marker 418, 518 corresponding to the first location and a second graphical marker 420, 520 corresponding to the second location. In certain embodiments, the at least one processor 132, 160, 170, 180 may be further configured to update the first graphical marker 418, 518 corresponding to the target placement location as the first location is tracked by the at least one processor and update the second graphical marker 420, 520 corresponding to the catheter 610 as the second location is tracked by the at least one processor. In certain embodiments, the first indication is a first graphical marker 418, 518 and the second indication is a second graphical marker 420, 520. In a representative embodiment, the at least one processor 132, 160, 170, 180 is further configured to dynamically update the first graphical marker 418, 518 as the target placement location is updated and the second graphical marker 420, 520 as the catheter 610 moves towards the target placement location. In certain embodiments, the at least one processor 132, 190 may be configured to provide a visual or auditory notification when the second location matches the first location.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for automatically acquiring and rotating an ultrasound volume based on a localized target structure.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method for placement of a medical device in an anatomical structure comprising:
   performing, by an ultrasound probe of an ultrasound system, one or more ultrasound image acquisitions;
   detecting and tracking, by at least one processor of the ultrasound system, one or more anatomical structures in the one or more ultrasound image acquisitions;
   causing, by the at least one processor, a display system to present a volume of a region of interest within or surrounding the one or more anatomical structures in the one or more ultrasound image acquisitions;
   processing, by the at least one processor, the one or more ultrasound image acquisitions to identify a first location corresponding to a target placement location within the region of interest for a medical device;
   processing, by the at least one processor, the one or more ultrasound image acquisitions to identify a second location corresponding to a location of a catheter including the medical device; and
   outputting a signal, by the at least one processor, to deploy the medical device when the second location corresponding to the location of the catheter matches the first location corresponding to the target placement location for the medical device.

2. The method of claim 1, further comprising rendering the one or more ultrasound image acquisitions overlaid with a first graphical marker corresponding to the first location and a second graphical marker corresponding to the second location.

3. The method of claim 2, further comprising updating the first graphical marker corresponding to the target placement location as the first location is tracked by the at least one processor and updating the second graphical marker corresponding to the catheter as the second location is tracked by the at least one processor.

4. The method of claim 2, wherein the matching of the first location and the second location is indicated by the first graphical marker overlapping with the second graphical marker.

5. The method of claim 1, further comprising automatically deploying the medical device when the signal is output.

6. The method of claim 1, transmitting a notification to an operator to deploy the medical device when the signal is output.

7. The method of claim 1, wherein the one or more anatomical structures is a left atrial appendage (LAA).

8. An ultrasound system comprising:
   an ultrasound probe configured to perform one or more ultrasound image acquisitions; and
   at least one processor configured to:
      detect and track one or more anatomical structures in the one or more ultrasound image acquisitions;
      cause a display system to present a volume of a region of interest within or surrounding the one or more anatomical structures in the one or more ultrasound image acquisitions;
      process the one or more ultrasound image acquisitions to identify a first location corresponding to a target placement location within the region of interest for a medical device;
      process the one or more ultrasound image acquisitions to identify a second location corresponding to a location of a catheter including the medical device; and
      output a signal to deploy the medical device when the second location corresponding to the location of the catheter matches the first location corresponding to the target placement location for the medical device.

9. The system of claim 8, the at least one processor further configured to render the one or more ultrasound image acquisitions overlaid with a first graphical marker corresponding to the first location and a second graphical marker corresponding to the second location.

10. The system of claim 9, the at least one processor further configured to update the first graphical marker corresponding to the target placement location as the first location is tracked by the at least one processor and updating the second graphical marker corresponding to the catheter as the second location is tracked by the at least one processor.

11. The system of claim 9, the at least one processor further configured to match the first location and the second location is indicated by the first graphical marker overlapping with the second graphical marker.

12. The system of claim 8, the at least one processor further configured to automatically deploy the medical device when the signal is output.

13. The system of claim 8, the at least one processor further configured to transmit a notification to an operator to deploy the medical device when the signal is output.

14. The system of claim 8, wherein the one or more anatomical structures is a left atrial appendage (LAA).

15. An ultrasound system for medical device placement in an anatomical structure comprising:
   an ultrasound probe configured to perform one or more ultrasound image acquisitions; and
   at least one processor configured to:
      detect and track a left atrial appendage (LAA) in the one or more ultrasound image acquisitions;
      cause a display system to present a volume of a region of interest within or surrounding the LAA in the one or more ultrasound image acquisitions;
      process the one or more ultrasound image acquisitions to identify a first location corresponding to a target placement location within the region of interest for a medical device;
      process the one or more ultrasound image acquisitions to identify a second location corresponding to a location of a catheter including the medical device;
      render the one or more ultrasound image acquisitions with a first indication of the first location and a second indication of the second location; and
      output a signal to automatically deploy the medical device when the second location corresponding to the location of the catheter matches the first location corresponding to the target placement location for the medical device.

16. The ultrasound system of claim 15, the at least one processor further configured to overlay the one or more ultrasound image acquisitions with a first graphical marker corresponding to the first location and a second graphical marker corresponding to the second location.

17. The ultrasound system of claim 16, the at least one processor further configured to update the first graphical marker corresponding to the target placement location as the first location is tracked by the at least one processor and update the second graphical marker corresponding to the catheter as the second location is tracked by the at least one processor.

18. The ultrasound system of claim 15, wherein the first indication is a first graphical marker and the second indication is a second graphical marker.

19. The ultrasound system of claim 15, the at least one processor further configured to dynamically update the first graphical marker as the target placement location is updated and the second graphical marker as the catheter moves towards the target placement location.

20. The ultrasound system of claim 15, the at least one processor further configured to provide a visual or auditory notification when the second location matches the first location.

\* \* \* \* \*